(12) United States Patent
Fujimoto et al.

(10) Patent No.: US 12,121,389 B2
(45) Date of Patent: Oct. 22, 2024

(54) CONTROL DEVICE, CONTROL METHOD, AND CONTROL PROGRAM

(71) Applicant: FUJIFILM CORPORATION, Tokyo (JP)

(72) Inventors: Yoshie Fujimoto, Kanagawa (JP); Shinichiro Konno, Kanagawa (JP); Shunsuke Kodaira, Kanagawa (JP)

(73) Assignee: FUJIFILM CORPORATION, Tokyo (JP)

( * ) Notice: Subject to any disclaimer, the term of this patent is extended or adjusted under 35 U.S.C. 154(b) by 371 days.

(21) Appl. No.: 17/486,955

(22) Filed: Sep. 28, 2021

(65) Prior Publication Data

US 2022/0096037 A1  Mar. 31, 2022

(30) Foreign Application Priority Data

Sep. 30, 2020 (JP) ................................ 2020-166468

(51) Int. Cl.
*A61B 6/00* (2024.01)
*A61B 6/04* (2006.01)
*A61B 6/08* (2006.01)
*A61B 6/50* (2024.01)
(Continued)

(52) U.S. Cl.
CPC .............. *A61B 6/54* (2013.01); *A61B 6/0414* (2013.01); *A61B 6/08* (2013.01); *A61B 6/502* (2013.01)

(58) Field of Classification Search
CPC ........... A61B 6/54; A61B 6/0414; A61B 6/08; A61B 6/502
See application file for complete search history.

(56) References Cited

U.S. PATENT DOCUMENTS

| 7,545,908 B2 * | 6/2009 | Hemmendorff ........ A61B 6/502 378/205 |
| 11,918,400 B2 * | 3/2024 | Fujimoto .................. A61B 6/54 |
| 2008/0080667 A1 | 4/2008 | Kashiwagi |

(Continued)

FOREIGN PATENT DOCUMENTS

| JP | 2007-236805 A | 9/2007 |
| JP | 2008-086383 A | 4/2008 |

(Continued)

OTHER PUBLICATIONS

English language translation of the following: Office action dated May 9, 2023 from the JPO in a Japanese patent application No. 2020-166468 corresponding to the instant patent application. This office action translation is submitted now in order to supplement the understanding of the cited references which are being disclosed in the instant Information Disclosure Statement.

(Continued)

*Primary Examiner* — Baisakhi Roy
(74) *Attorney, Agent, or Firm* — SOLARIS Intellectual Property Group, PLLC

(57) ABSTRACT

A control device including: at least one processor, wherein the processor is configured to detect whether or not a compression member which compresses a breast is attached to a main body of a mammography apparatus and control an image projection unit which projects a projection image onto a projection surface of the compression member such that the projection image is projected onto the projection surface in a case in which it is detected that the compression member is attached.

13 Claims, 9 Drawing Sheets

(51) Int. Cl.
*G03B 21/20* (2006.01)
*G06T 7/00* (2017.01)

(56) References Cited

U.S. PATENT DOCUMENTS

| | | | |
|---|---|---|---|
| 2008/0087830 | A1 | 4/2008 | Kashiwagi |
| 2010/0054402 | A1 | 3/2010 | Fischer et al. |
| 2012/0155610 | A1 | 6/2012 | Murakoshi et al. |
| 2014/0294142 | A1 | 10/2014 | Choi |
| 2016/0256119 | A1* | 9/2016 | Nakayama ............... A61B 6/50 |
| 2017/0172531 | A1 | 6/2017 | Sugiyama et al. |
| 2017/0367671 | A1* | 12/2017 | Arai ........................ A61B 6/502 |
| 2017/0367674 | A1* | 12/2017 | Arai ........................ A61B 6/54 |
| 2017/0367675 | A1* | 12/2017 | Arai ........................ A61B 6/502 |
| 2021/0298696 | A1* | 9/2021 | Paige ................... A61B 6/0414 |
| 2022/0031262 | A1* | 2/2022 | Cowles ................. A61B 6/462 |
| 2023/0005149 | A1* | 1/2023 | Nakayama ............... G06T 7/90 |

FOREIGN PATENT DOCUMENTS

| | | |
|---|---|---|
| JP | 2008-086389 A | 4/2008 |
| JP | 2008-203393 A | 9/2008 |
| JP | 2009-291336 A | 12/2009 |
| JP | 2010-253263 A | 11/2010 |
| JP | 2011-104149 A | 6/2011 |
| JP | 2012-010963 A | 1/2012 |
| JP | 2012-143549 A | 8/2012 |
| JP | 2014-233318 A | 12/2014 |
| JP | 2017-113540 A | 6/2017 |
| JP | 2017-225634 A | 12/2017 |
| JP | 2018-175238 A | 11/2018 |

OTHER PUBLICATIONS

English language translation of the following: Office action dated Aug. 29, 2023 from the JPO in a Japanese patent application No. 2020-166468 corresponding to the instant patent application.

\* cited by examiner

CONTROL DEVICE, CONTROL METHOD, AND CONTROL PROGRAM

CROSS-REFERENCE TO RELATED APPLICATION

The present application claims priority under 35 U.S.C. § 119 to Japanese Patent Application No. 2020-166468 filed on Sep. 30, 2020. The above application is hereby expressly incorporated by reference, in its entirety, into the present application.

BACKGROUND

Technical Field

The present disclosure relates to a control device, a control method, and a non-transitory computer-readable storage medium storing a control program.

Description of the Related Art

A mammography apparatus is known which irradiates a breast compressed by a compression member with radiation to capture a radiographic image. In a case in which imaging is performed, information or the like for assisting the imaging may be displayed. For example, JP2008-086389A discloses a technique that displays a skin line of the breast on a liquid crystal display (LCD) and displays a projection image thereof on a projection surface of a compression member.

However, in a case in which the projection image is automatically projected onto the projection surface of the compression member regardless of the instruction of the user, the timing when projection is started may be inappropriate. For example, in a case in which the projection image is projected in a state in which the compression member is not attached to the main body of the mammography apparatus, the projection image is projected onto an imaging table. Therefore, it may be difficult for the user who performs positioning to understand the projection image.

The present disclosure has been made in view of the above-mentioned problems, and an object of the present disclosure is to provide a control device, a control method, and a non-transitory computer-readable storage medium storing a control program that can project a projection image onto a projection surface of a compression member at an appropriate timing.

SUMMARY

In order to achieve the above object, according to a first aspect of the present disclosure, there is provided a control device comprising at least one processor. The processor detects whether or not a compression member which compresses a breast is attached to a main body of a mammography apparatus and controls an image projection unit which projects a projection image onto a projection surface of the compression member such that the projection image is projected onto the projection surface in a case in which it is detected that the compression member is attached.

In addition, in order to achieve the above object, according to a second aspect of the present disclosure, there is provided a control device comprising at least one processor. The processor detects whether or not a compression member which compresses a breast is attached to a main body of a mammography apparatus and controls an image projection unit which projects a projection image onto a projection surface of the compression member such that the projection image is not projected onto the projection surface in a case in which it is detected that the compression member is not attached.

According to a third aspect of the present disclosure, in the control device according to the first aspect, the processor may further detect whether or not the compression member starts to move in a direction in which the breast is compressed and performs control to project the projection image onto the projection surface in a case in which it is detected that the compression member is attached and starts to move.

According to a fourth aspect of the present disclosure, in the control device according to the first aspect, the processor may instruct the mammography apparatus on an imaging menu related to the capture of an image of the breast and perform control to project the projection image onto the projection surface in a case in which the compression member is attached and the mammography apparatus is instructed on the imaging menu.

According to a fifth aspect of the present disclosure, in the control device according to the first aspect, the processor may receive a projection start instruction to start the projection of the projection image onto the projection surface and perform control to project the projection image onto the projection surface in a case in which the compression member is attached and the projection start instruction is received.

According to a sixth aspect of the present disclosure, in the control device according to the first aspects, the processor may receive a projection end instruction to end the projection of the projection image onto the projection surface and perform control not to project the projection image onto the projection surface in a case in which the projection end instruction is received.

According to a seventh aspect of the present disclosure, in the control device according to any one of the first to sixth aspects, after controlling the image projection unit such that the projection image is capable of being projected, the processor may perform control to project the projection image onto the projection surface.

According to an eighth aspect of the present disclosure, in the control device according to the first aspect, in a case in which the mammography apparatus captures each of a series of a plurality of radiographic images, the processor may perform control to project, onto the projection surface, the projection image corresponding to each imaging operation, which corresponds to each of the plurality of radiographic images, in each imaging operation.

According to a ninth aspect of the present disclosure, in the control device according to the first aspect, the processor may further detect a type of the compression member attached to the main body of the mammography apparatus and may not perform control to project the projection image onto the projection surface in a case in which the detected type is a type onto which the projection of the projection image is not permitted.

According to a tenth aspect of the present disclosure, in the control device according to the first aspect, the processor may further detect a type of the compression member attached to the main body of the mammography apparatus and perform control to project the projection image onto the projection surface in a case in which the detected type is a type onto which the projection of the projection image is permitted.

Further, in order to achieve the above object, according to an eleventh aspect of the present disclosure, there is provided a control method comprising: detecting whether or not a compression member which compresses a breast is attached to a main body of a mammography apparatus; and controlling an image projection unit which projects a projection image onto a projection surface of the compression member such that the projection image is projected onto the projection surface in a case in which it is detected that the compression member is attached.

Further, in order to achieve the above object, according to a twelfth aspect of the present disclosure, there is provided a control method comprising: detecting whether or not a compression member which compresses a breast is attached to a main body of a mammography apparatus; and controlling an image projection unit which projects a projection image onto a projection surface of the compression member such that the projection image is not projected onto the projection surface in a case in which it is detected that the compression member is not attached.

Further, in order to achieve the above object, according to a thirteenth aspect of the present disclosure, there is provided a non-transitory computer-readable storage medium storing a control program that causes a computer to perform a process comprising: detecting whether or not a compression member which compresses a breast is attached to a main body of a mammography apparatus; and controlling an image projection unit which projects a projection image onto a projection surface of the compression member such that the projection image is projected onto the projection surface in a case in which it is detected that the compression member is attached.

Further, in order to achieve the above object, according to a fourteenth aspect of the present disclosure, there is provided a non-transitory computer-readable storage medium storing a control program that causes a computer to perform a process comprising: detecting whether or not a compression member which compresses a breast is attached to a main body of a mammography apparatus; and controlling an image projection unit which projects a projection image onto a projection surface of the compression member such that the projection image is not projected onto the projection surface in a case in which it is detected that the compression member is not attached.

According to the present disclosure, it is possible to project the projection image onto the projection surface of the compression member at an appropriate timing.

BRIEF DESCRIPTION OF THE DRAWINGS

Exemplary embodiments according to the technique of the present disclosure will be described in detail based on the following figures, wherein.

DETAILED DESCRIPTION

Hereinafter, embodiments of the present disclosure will be described in detail with reference to the drawings. In addition, each of the embodiments does not limit the present disclosure.

First Embodiment

Figure 1:
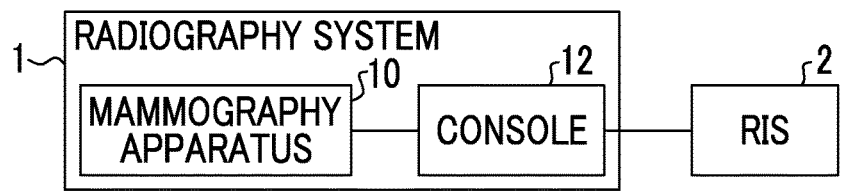
FIG. 1 is a diagram schematically illustrating an example of the overall configuration of a radiography system according to an embodiment.

First, an example of the overall configuration of a radiography system according to an embodiment will be described. FIG. 1 is a diagram illustrating an example of the overall configuration of a radiography system 1 according to this embodiment. As illustrated in FIG. 1, the radiography system 1 according to this embodiment comprises a mammography apparatus 10 and a console 12. The mammography apparatus 10 according to this embodiment is an example of a radiography apparatus according to the present disclosure. Further, the console 12 according to this embodiment is an example of a control device according to the present disclosure.

Figure 2A:
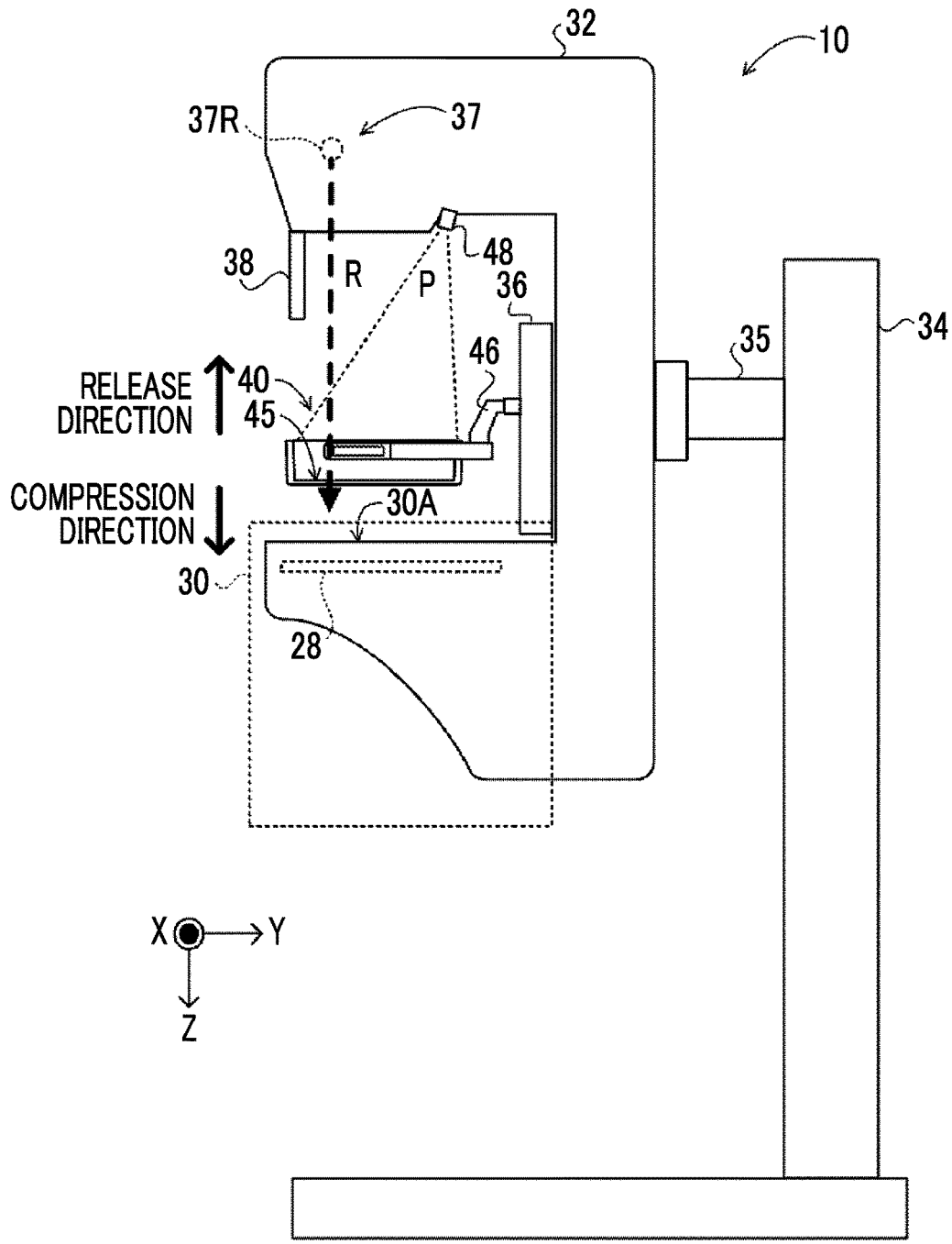
FIG. 2A is a side view illustrating an example of the outward appearance of a mammography apparatus according to the embodiment.
Figure 3:
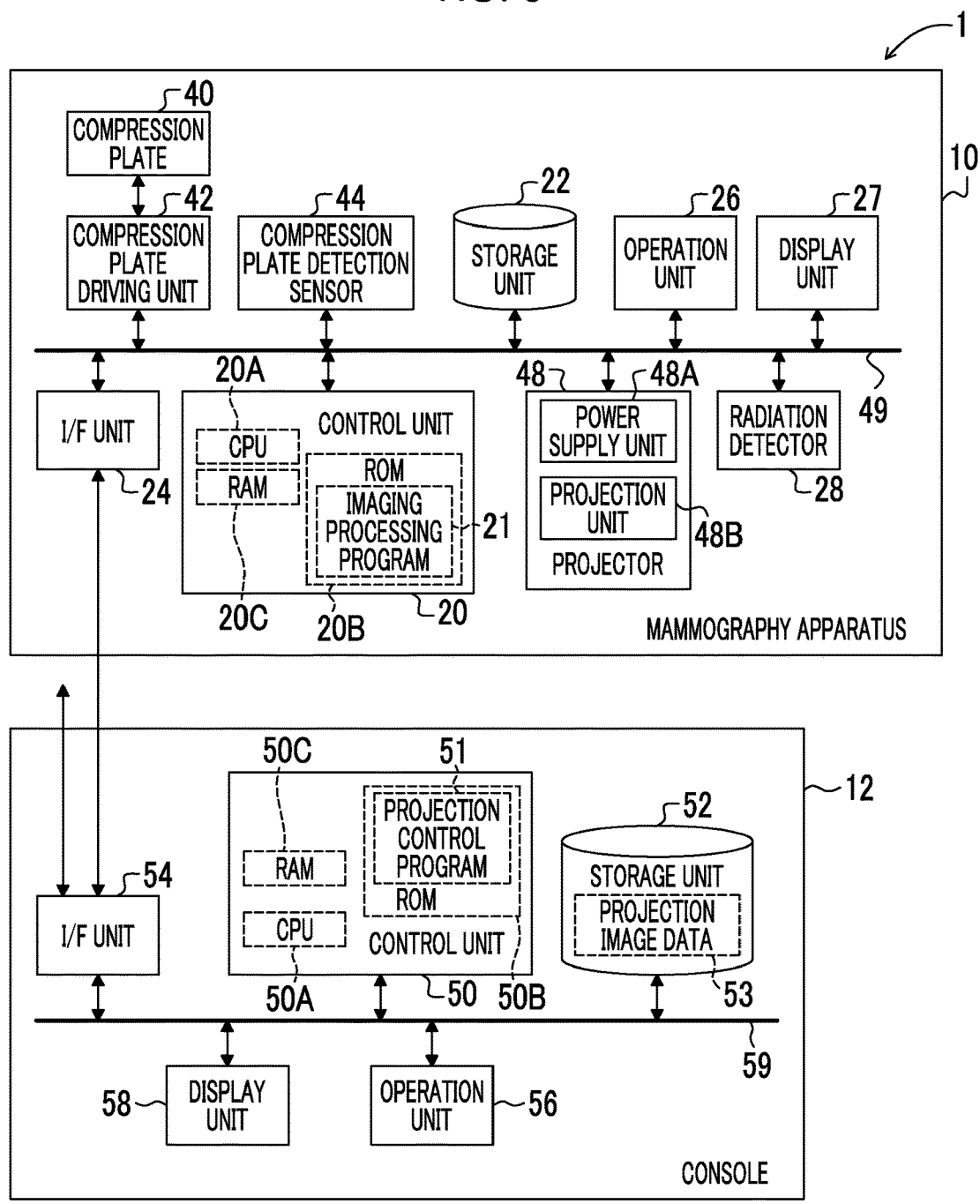
FIG. 3 is a block diagram illustrating an example of the configuration of the mammography apparatus and a console according to the embodiment.

First, the mammography apparatus 10 according to this embodiment will be described. FIG. 2A is a side view illustrating an example of the outward appearance of the mammography apparatus 10 according to this embodiment. In addition, FIG. 2A illustrates an example of the outward appearance of the mammography apparatus 10 as viewed from the right side of a subject. Further, FIG. 3 is a functional block diagram illustrating an example of the configuration of the mammography apparatus 10 and the console 12 according to this embodiment.

The mammography apparatus 10 according to this embodiment irradiates a breast of the subject as an object with radiation R (for example, X-rays) to capture a radiographic image of the breast. In addition, the mammography apparatus 10 may be an apparatus that captures the image of the breast of the subject not only in a state in which the subject is standing (standing state) but also in a state in which the subject is sitting, for example, on a chair (including a wheelchair) (sitting state).

A radiation detector 28 detects the radiation R transmitted through the breast. As illustrated in FIG. 2A, the radiation detector 28 is disposed in an imaging table 30. In the mammography apparatus 10 according to this embodiment, in a case in which imaging is performed, the breast of the subject is positioned on an imaging surface 30A of the imaging table 30 by a user.

The radiation detector 28 detects the radiation R transmitted through the breast of the subject and the imaging table 30, generates a radiographic image on the basis of the detected radiation R, and outputs image data indicating the generated radiographic image. The type of the radiation detector 28 according to this embodiment is not particularly limited. For example, the radiation detector 28 may be an indirect-conversion-type radiation detector that converts the radiation R into light and converts the converted light into charge or a direct-conversion-type radiation detector that directly converts the radiation R into charge.

A radiation emitting unit 37 comprises a radiation source 37R. As illustrated in FIG. 2A, the radiation emitting unit 37 is provided in an arm portion 32 together with the imaging table 30 and a compression unit 36. As illustrated in FIG. 2A, a face guard 38 is attachably and detachably provided at a position of the arm portion 32 which is close to the subject below the radiation emitting unit 37. The face guard 38 is a protective member for protecting the subject from the radiation R emitted from the radiation source 37R.

In addition, as illustrated in FIG. 2A, the mammography apparatus 10 according to this embodiment comprises the arm portion 32, a base 34, and a shaft portion 35. The arm portion 32 is held by the base 34 so as to be movable in the up-down direction (Z-axis direction). The shaft portion 35 connects the arm portion 32 to the base 34. In addition, the arm portion 32 can be relatively rotated with respect to the base 34, using the shaft portion 35 as a rotation axis.

In the mammography apparatus 10 according to this embodiment, at least two types of imaging can be performed to capture radiographic images. Specifically, the mammography apparatus 10 can perform at least two types of imaging, that is, cranio-caudal (CC) imaging in which the imaging direction is a cranio-caudal direction and mediolateral oblique (MLO) imaging in which the imaging direction is a medio-lateral oblique direction for the breast. In the following description, the position of the radiation source 37R in a case in which the radiation R is emitted from the radiation source 37R to the imaging table 30 in the capture of a radiographic image is referred to as an "imaging position".

In a case in which the CC imaging is performed, the imaging surface 30A is adjusted to a state in which the imaging surface 30A faces the upper side of the mammography apparatus 10 (the head of the subject). Further, in this case, the position of the radiation source 37R is adjusted to the imaging position that faces the imaging surface 30A of the imaging table 30. Therefore, the radiation R is emitted from the radiation source 37R to the breast in a direction from the head to the foot of the subject, and the CC imaging is performed.

In contrast, in a case in which the MLO imaging is performed, the position of the imaging table 30 is adjusted to a state in which the imaging surface 30A is rotated up to a predetermined angle in a range of, for example, 45 degrees or more and less than 90 degrees with respect to the case in which the CC imaging is performed. Specifically, in a case in which an image of the left breast is captured, the imaging surface 30A is inclined to the right. In a case in which an image of the right breast is captured, the imaging surface 30A is inclined to the left. Therefore, the radiation R is emitted from the radiation source 37R to the breast in a direction from the center of the body of the subject to the outside (in a direction from a space between the breasts of the subject to the arm), and the MLO imaging is performed.

The compression unit 36 connected to the arm portion 32 is provided with a compression plate driving unit (see a compression plate driving unit 42 in FIG. 3) that moves a compression plate 40 compressing the breast in an up-down direction (Z-axis direction). A support portion 46 of the compression plate 40 is detachably attached to the compression plate driving unit 42. The compression plate 40 attached to the compression plate driving unit 42 is moved in the up-down direction (Z-axis direction) by the compression plate driving unit to compress the breast of the subject between the compression plate 40 and the imaging table 30. As illustrated in FIG. 2A, for the movement direction of the compression plate 40, the direction in which the breast is compressed, that is, the direction in which the compression plate 40 approaches the imaging surface 30A is referred to as a "compression direction", and the direction in which the compression of the breast is released, that is, the direction in which the compression plate 40 approaches the radiation emitting unit 37 is referred to as a "release direction".

A compression plate identifier (not illustrated) for identifying the type of the compression plate 40 (which will be described in detail below) is provided in the support portion 46 of the compression plate 40 on the side attached to the compression plate driving unit 42. The compression unit 36 is provided with a compression plate detection sensor (see a compression plate detection sensor 44 in FIG. 3). The compression plate detection sensor 44 reads the compression plate identifier provided in the support portion 46 of the compression plate 40 to detect the type of the attached compression plate 40. In addition, the compression plate 40 according to this embodiment is an example of a compression member according to the present disclosure.

There are a plurality of types of compression plates 40 that can be attached to the mammography apparatus 10 according to this embodiment. In this example, the compression plate 40 compresses the entire breast. However, the present disclosure is not limited thereto. For example, a compression plate 40 that compresses a portion of the breast may be used. In other words, the compression plate 40 may be smaller than the breast. For example, as the compression plate 40, a compression plate 40 is known which is used for so-called spot imaging that captures a radiographic image of only the region in which a lesion is present. Further, other types of compression plates 40 include, for example, a compression plate corresponding to the size of the breast, a compression plate for axillary imaging, and a compression plate for enlargement imaging. Further, although the compression plate 40 is referred to as a "compression plate" for convenience, it is not limited to a plate-shaped member. For example, the compression plate 40 may be a film-shaped member.

Figure 2B:
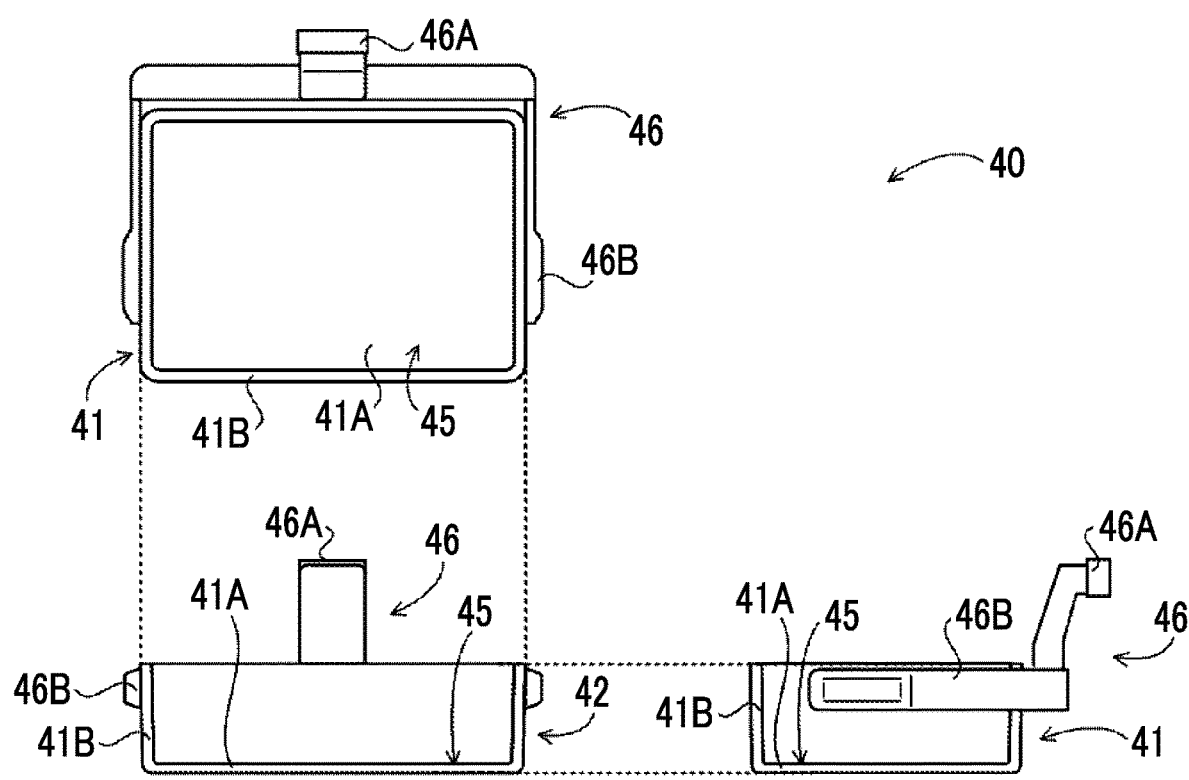
FIG. 2B is a three-view diagram illustrating an example of a compression plate according to the embodiment.

As a specific example, the compression plate 40 that can be attached to the mammography apparatus 10 according to this embodiment will be described with reference to FIG. 2B. FIG. 2B is a three-view diagram illustrating an example of the compression plate 40 according to this embodiment. The three-view diagram illustrated in FIG. 2B includes a plan view (top view) of the compression plate 40 viewed from the upper side (from the radiation emitting unit 37), a side view of the compression plate 40 viewed from the subject, and a side view of the compression plate 40 viewed from the right side of the subject. As illustrated in FIG. 2B, the compression plate 40 according to this embodiment includes a compression portion 41 and a support portion 46.

The compression portion 41 is formed in a concave shape in a cross-sectional view in which a bottom portion 41A is surrounded by a wall portion 41B. In the bottom portion 41A, the thickness of a plate having a surface that comes into contact with the breast of the subject is substantially constant, and a surface that faces the radiation source 37R is flat and has a substantially uniform height. Further, the wall portion 41B is relatively high and has a substantially uniform height. The compression portion 41 has a projection surface 45 onto which a projection image P is projected by a projector 48 which will be described below. For example, in this embodiment, a surface (upper surface) of the bottom portion 41A of the compression portion 41 which faces the radiation emitting unit 37 is the projection surface 45. In addition, for example, the position of the projection surface 45 of the compression plate 40 is not limited to this aspect. For example, the projection surface 45 may be a surface of the bottom portion 41A of the compression portion 41 which comes into contact with the breast or a surface of the wall portion 41B.

It is preferable that the compression plate 40 is optically transparent in order to check positioning or a compressed state. In addition, the compression plate 40 is made of a material having high transmittance for the radiation R. Further, in a case in which light is incident on the projection surface 45, most of the light (for example, 90%) is transmitted and a portion (for example, 10%) of the light is specularly reflected from the surface of an object such that an incident angle and a reflection angle are equal to each other, in order to display an image corresponding to the projection image P projected from the projector 48. For example, a surface of the bottom portion 41A of the compression plate 40 which faces the radiation source 37R may be roughened to form the projection surface 45. In addition, for example, a specular reflection sheet may be attached to the surface of the compression plate 40 to form the projection surface 45. Further, in a case in which the projection surface 45 is a smooth surface such as a case in which a specular reflection sheet is attached, a surface of the compression plate 40 that comes into contact with the subject, such as the breast, may be the projection surface 45.

On the other hand, the support portion 46 includes an attachment portion 46A and an arm 46B. The attachment portion 46A has a function of attaching the compression plate 40 to the mammography apparatus 10, specifically, the compression plate driving unit 42 in the compression unit 36. The arm 46B has a function of supporting the compression portion 41.

Further, the projector 48 that projects the projection image P onto the projection surface 45 of the compression plate 40 is provided at a position of the arm portion 32 which is away from the subject below the radiation emitting unit 37. The projector 48 according to this embodiment is an example of an image projection unit according to the present disclosure. Known projectors, such as a liquid crystal projector, a Digital Light Processing (DLP) (registered trademark) projector, and a laser projector, can be used as the projector 48. As illustrated in FIG. 3, the projector 48 according to this embodiment includes a power supply unit 48A and a projection unit 48B. In the projector 48, the turn-on and turn-off of the power supply unit 48A are controlled in response to an instruction from a control unit 20 which will be described below. Further, the projection image P is projected from the projection unit 48B onto the projection surface 45 of the compression plate 40 in response to an instruction from the control unit 20.

Furthermore, the control unit 20, a storage unit 22, an interface (I/F) unit 24, an operation unit 26, and a display unit 27 illustrated in FIG. 3 are provided in the imaging table 30 of the mammography apparatus 10 according to this embodiment. The control unit 20, the storage unit 22, the I/F unit 24, the operation unit 26, the display unit 27, the radiation detector 28, the compression plate driving unit 42, the compression plate detection sensor 44, and the projector 48 are connected to each other through a bus 49, such as a system bus or a control bus, such that they can transmit and receive various kinds of information.

The control unit 20 controls the overall operation of the mammography apparatus 10 under the control of the console 12. The control unit 20 includes a central processing unit (CPU) 20A, a read only memory (ROM) 20B, and a random access memory (RAM) 20C. For example, various programs including an imaging processing program 21 which is executed by the CPU 20A and performs control related to the capture of a radiographic image are stored in the ROM 20B in advance. The RAM 20C temporarily stores various kinds of data.

For example, image data of the radiographic image captured by the radiation detector 28 and various other kinds of information are stored in the storage unit 22. Specific examples of the storage unit 22 include a hard disk drive (HDD) and a solid state drive (SSD). The I/F unit 24 transmits and receives various kinds of information to and from the console 12 using wireless communication or wired communication. The image data of the radiographic image captured by the radiation detector 28 in the mammography apparatus 10 is transmitted to the console 12 through the I/F unit 24 by wireless communication or wired communication.

In addition, the operation unit 26 is provided as a plurality of switches in, for example, the imaging table 30 of the mammography apparatus 10. Further, the operation unit 26 according to this embodiment includes at least a compression instruction button for instructing the movement of the compression plate 40 in the compression direction and a release button for instructing the movement of the compression plate 40 in the release direction. The operation unit 26 may be provided as a touch panel switch or may be provided as a foot switch that is operated by the feet of the user such as a doctor or a radiology technician. The display unit 27 displays various kinds of information related to the subject or imaging.

The console 12 according to this embodiment has a function of controlling the mammography apparatus 10 using, for example, an imaging order and various kinds of information acquired from a radiology information system (RIS) 2 through a wireless communication local area network (LAN) and instructions input by the user through an operation unit 56 or the like.

For example, the console 12 according to this embodiment is a server computer. As illustrated in FIG. 3, the console 12 comprises a control unit 50, a storage unit 52, an I/F unit 54, the operation unit 56, and a display unit 58. The control unit 50, the storage unit 52, the I/F unit 54, the operation unit 56, and the display unit 58 are connected to each other through a bus 59, such as a system bus or a control bus, such that they can transmit and receive various kinds of information.

The control unit 50 according to this embodiment controls the overall operation of the console 12. The control unit 50 comprises a CPU 50A, a ROM 50B, and a RAM 50C. For example, various programs including a projection control program 51 (which will be described below) executed by the CPU 50A are stored in the ROM 50B in advance. The RAM 50C temporarily stores various kinds of data. The CPU 50A according to this embodiment is an example of a processor according to the present disclosure. The projection control program 51 according to this embodiment is an example of a control program according to the present disclosure.

The storage unit 52 stores, for example, projection image data 53, the image data of the radiographic image captured by the mammography apparatus 10, and various other kinds of information. An HDD or an SSD is given as a specific example of the storage unit 52.

The operation unit 56 is used by the user to input, for example, instructions which are related to the capture of a radiographic image and include an instruction to emit the radiation R or various kinds of information. The operation unit 56 is not particularly limited. Examples of the operation unit 56 include various switches, a touch panel, a touch pen, and a mouse. The display unit 58 displays various kinds of information. In addition, the operation unit 56 and the display unit 58 may be integrated into a touch panel display.

The I/F unit 54 transmits and receives various kinds of information between the mammography apparatus 10 and the RIS 2 using wireless communication or wired communication. In the radiography system 1 according to this embodiment, the console 12 receives the image data of the radiographic image captured by the mammography apparatus 10 from the mammography apparatus 10 through the I/F unit 54, using wireless communication or wired communication.

Figure 4:
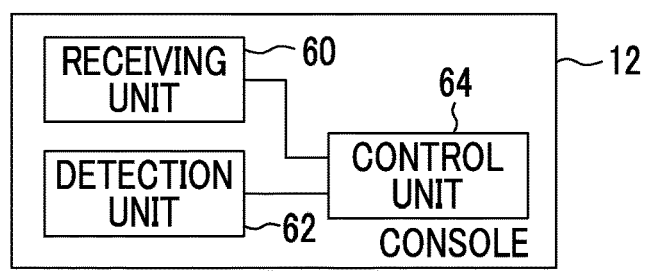
FIG. 4 is a functional block diagram illustrating an example of the function of the console according to the embodiment.

In addition, FIG. 4 is a functional block diagram illustrating an example of the configuration of the console 12 according to this embodiment. As illustrated in FIG. 4, the console 12 comprises a receiving unit 60, a detection unit 62, and a control unit 64. For example, in the console 12 according to this embodiment, the CPU 50A of the control unit 50 executes the projection control program 51 stored in the ROM 50B to function as the receiving unit 60, the detection unit 62, and the control unit 64.

The receiving unit 60 has a function of receiving a projection end instruction to end the projection of the projection image P onto the projection surface 45. For example, in this embodiment, in a case in which the user wants to end the projection of the projection image P onto the projection surface 45, the user inputs a projection end instruction through the operation unit 26 of the mammography apparatus 10. The mammography apparatus 10 outputs a projection end instruction signal through the I/F unit 24. In a case in which the projection end instruction signal is input to the console 12, the receiving unit 60 receives the projection end instruction to end the projection of the projection image P. The receiving unit 60 outputs projection end information indicating that the projection end instruction has been received to the control unit 64.

The detection unit 62 has a function of detecting whether or not the compression plate 40 is attached to the main body of the mammography apparatus 10. For example, in this embodiment, as described above, in the mammography apparatus 10, the compression plate detection sensor 44 reads the compression plate identifier of the compression plate 40 having the support portion 46 attached to the compression unit 36. Then, the detection unit 62 according to this embodiment outputs an instruction signal for reading the compression plate identifier to the mammography apparatus 10 through the I/F unit 54. In the mammography apparatus 10, the control unit 20 directs the compression plate detection sensor 44 to read the compression plate identifier in response to the input instruction signal and outputs the read compression plate identifier to the console 12 through the I/F unit 24. In addition, in a case in which the compression plate 40 is not attached to the compression unit 36 of the mammography apparatus 10 and the compression plate detection sensor 44 is not capable of reading the compression plate identifier, the control unit 20 directs the compression plate detection sensor 44 to repeat the operation of reading the compression plate identifier at predetermined intervals.

In a case in which the compression plate identifier output from the mammography apparatus 10 is input to the console 12, the detection unit 62 detects that the compression plate 40 is attached to the main body of the mammography apparatus 10. In a case in which the detection unit 62 detects that the compression plate 40 is attached to the main body of the mammography apparatus 10, it outputs the compression plate identifier to the control unit 64.

Further, the detection unit 62 according to this embodiment has a function of detecting whether or not the compression plate 40 starts to move in the compression direction in which the breast is compressed. For example, in this embodiment, in a case in which the compression plate driving unit 42 of the mammography apparatus 10 starts to move the compression plate 40 in the compression direction, the control unit 20 outputs a compression movement start signal indicating the fact to the console 12 through the I/F unit 24. In a case in which the compression movement start signal output from the mammography apparatus 10 is input to the console 12, the detection unit 62 detects that the compression plate 40 starts to move in the compression direction. In a case in which the detection unit 62 detects that the compression plate 40 starts to move in the compression direction, it outputs compression movement start information indicating the fact to the control unit 64.

The control unit 64 has a function of performing control to project the projection image P onto the projection surface 45 in a case in which the detection unit 62 detects that the compression plate 40 is attached and starts to move in the compression direction. Specifically, in a case in which the compression plate identifier and the compression movement start information are input from the detection unit 62, the control unit 64 outputs a start control signal for directing the projector 48 to start the projection of the projection image P and the projection image data 53 indicating the projection image P to the mammography apparatus 10 through the I/F unit 54.

More specifically, in a case in which the compression plate identifier is input from the detection unit 62, the control unit 64 according to this embodiment acquires the projection image data 53 indicating the projection image P corresponding to the compression plate identifier from the storage unit 52. A projection image for guiding the positioning of the breast is applied as the projection image P according to this embodiment. Specifically, a projection image projected from the projector 48 in order to display an image for guiding at least one of the shape or position of the breast compressed by the compression plate 40 on the projection surface 45 of the compression plate 40 is applied as the projection image P. For example, in this embodiment, an image indicating the skin line of the breast and the position of the nipple in a case in which a standard breast corresponding to the type of the compression plate 40 or the like is compressed to an ideal state is applied as the image for guiding at least one of the shape or position of the breast.

In some cases, the size of the compression portion 41 and the size of the projection surface 45 vary depending on the type of the compression plate 40. Therefore, in this embodiment, the projection image P corresponding to the type of the compression plate 40 is projected from the projector 48. For example, in this embodiment, a plurality of projection image data items indicating the projection images P corresponding to the types of the compression plates 40 are stored as the projection image data 53 in the storage unit 52 so as to be associated with the compression plate identifiers. The control unit 64 acquires the projection image data 53 corresponding to the compression plate identifier input from the detection unit 62 from the storage unit 52 and outputs the projection image data 53 to the mammography apparatus 10 through the I/F unit 54.

Further, in a case in which the compression movement start information is input after the compression plate identifier is input from the detection unit 62, the control unit 64 outputs the start control signal for directing the projector 48 to start the projection of the projection image P to the mammography apparatus 10 through the I/F unit 54.

In addition, the control unit 64 according to this embodiment has a function of performing control to end the projection of the projection image P by the projector 48 in a case in which the receiving unit 60 receives the instruction to end the projection of the projection image P. Specifically, in a case in which the projection end information is input from the receiving unit 60, the control unit 64 outputs an end control signal for ending the projection of the projection image P by the projector 48 to the mammography apparatus 10 through the I/F unit 54.

Figure 5:
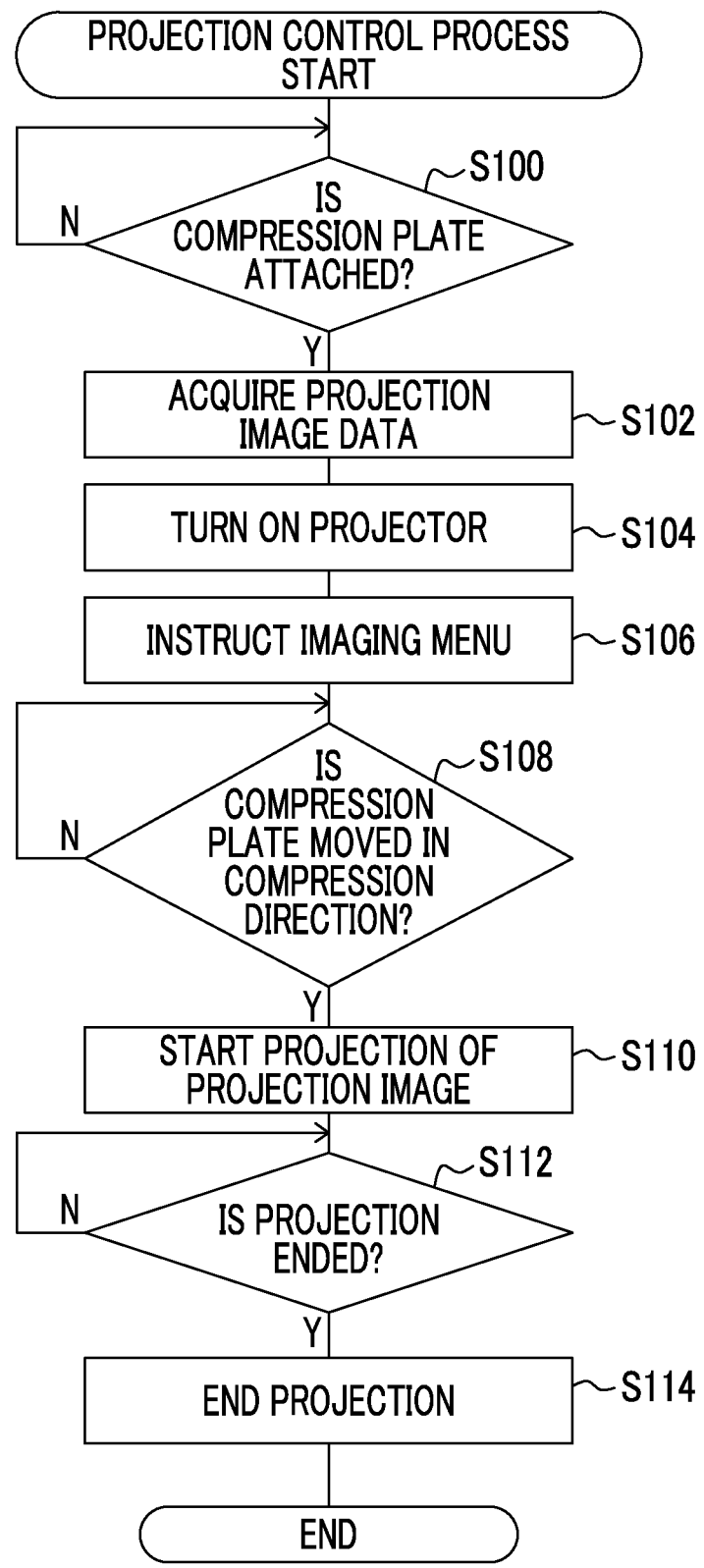
FIG. 5 is a flowchart illustrating an example of the flow of a projection control process according to a first embodiment.

Next, the operation of the console 12 in the projection of the projection image P by the mammography apparatus 10 according to this embodiment will be described with reference to the drawings. The console 12 displays a plurality of types of imaging menus prepared in advance on the display unit 58 such that one of the menus can be selected. The user selects one imaging menu that is matched with the content of the imaging order through the operation unit 56. The console 12 receives the imaging menu selected by the user. For example, in this embodiment, in a case in which the console 12 receives the selected imaging menu, a projection control process illustrated in FIG. 5 is performed. In the console 12 according to this embodiment, for example, the CPU 50A of the control unit 50 executes the projection control program 51 stored in the ROM 50B to perform the projection control process whose example is illustrated in FIG. 5. FIG. 5 is a flowchart illustrating an example of the flow of the projection control process performed in the console 12 according to this embodiment.

In Step S100 of FIG. 5, the detection unit 62 determines whether or not the compression plate 40 is attached to the main body of the mammography apparatus 10. As described above, the determination result in Step S100 is "No" until the compression plate identifier is input to the console 12. On the other hand, in a case in which the compression plate identifier is input to the console 12, the detection unit 62 detects that the compression plate 40 is attached to the main body of the mammography apparatus 10. Therefore, the determination result in Step S100 is "Yes", and the process proceeds to Step S102.

In Step S102, the control unit 64 acquires the projection image data 53 corresponding to the compression plate identifier from the storage unit 52 as described above. Then, in Step S104, the control unit 64 outputs a power-on instruction signal for turning on the projector 48 to the mammography apparatus 10 through the I/F unit 54. In the mammography apparatus 10, in a case in which the power-on instruction signal is input, the control unit 20 performs control such that power is supplied to the power supply unit 48A of the projector 48 to turn on the power supply unit 48A. That is, the mammography apparatus 10 changes to a state in which the projector 48 can project the projection image P.

Then, in Step S106, the control unit 64 instructs the mammography apparatus 10 on the imaging menu selected by the user through the I/F unit 54. The mammography apparatus 10 sets, for example, the tube voltage and mAs value of the radiation source 37R according to the instructed imaging menu.

Then, in Step S108, the detection unit 62 determines whether or not the compression plate 40 starts to move in the compression direction. As described above, the determination result in Step S108 is "No" until the compression movement start signal is input to the console 12. On the other hand, in a case in which the compression movement start signal is input to the console 12, the determination result in Step S108 is "Yes", and the process proceeds to Step S110.

Figure 6:
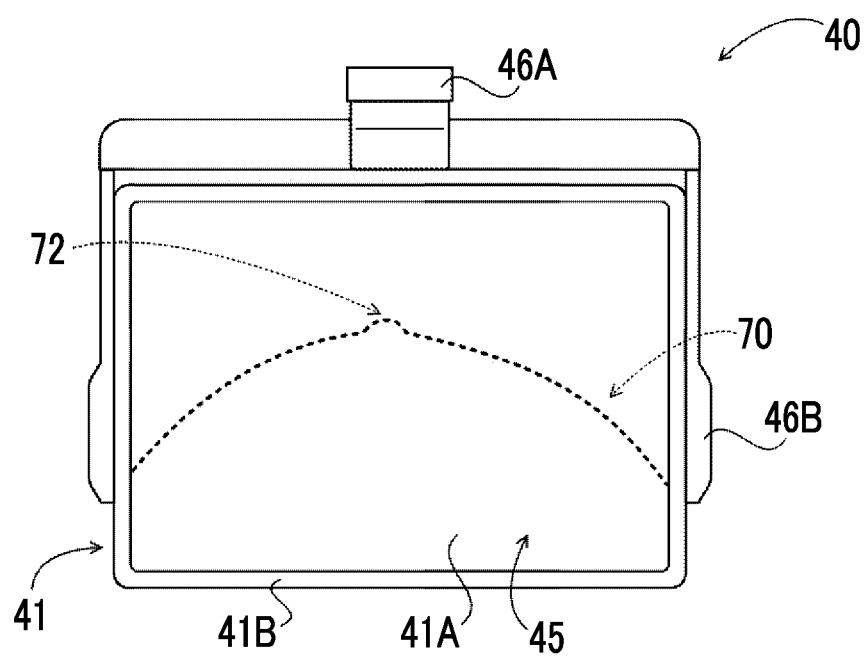
FIG. 6 is a diagram illustrating an example of a state displayed by a projection image projected onto a projection surface of the compression plate.

In Step S110, the control unit 64 outputs the projection image data 53 acquired in Step S102 to the mammography apparatus 10 through the I/F unit 54. In the mammography apparatus 10, in a case in which the projection image data 53 is input, the control unit 20 performs control to direct the projection unit 48B of the projector 48 to project the projection image P corresponding to the projection image data 53. A display image corresponding to the projection image P is displayed on the projection surface 45 of the compression plate 40 attached to the compression unit 36 of the mammography apparatus 10 by this control. In this embodiment, as described above, an image indicating the skin line of the breast and the position of the nipple is displayed on the projection surface 45 of the compression plate 40. FIG. 6 illustrates an example of a skin line 70 and a position 72 of the nipple displayed on the projection surface 45 of the compression plate 40. The user compresses the breast of the subject positioned with reference to the displayed skin line and the displayed position of the nipple with the compression plate 40.

In a case in which the compression of the breast is completed, the user inputs an instruction to emit the radiation R. In a case in which the mammography apparatus 10 receives an instruction to emit the radiation R, the radiation R is emitted from the radiation source 37R of the radiation emitting unit 37, and the radiation detector 28 captures a radiographic image of the breast.

As described above, the user inputs the projection end instruction to end the projection of the projection image P at any timing such as before the radiation R is emitted or after the capture of the radiographic image by the radiation detector 28 ends.

Then, in Step S112, the control unit 64 determines whether or not to end the projection of the projection image P. As described above, the determination result in Step S112 is "No" until the receiving unit 60 receives the projection end instruction signal. On the other hand, in a case in which the receiving unit 60 receives the projection end instruction signal, the determination result in Step S112 is "Yes", and the process proceeds to Step S114.

In Step S114, as described above, the control unit 64 outputs the end control signal for ending the projection of the projection image P by the projector 48 to the mammography apparatus 10 through the I/F unit 54 and then ends the projection control process illustrated in FIG. 5. In the mammography apparatus 10, in a case in which the end control signal is input, the control unit 20 ends the projection of the projection image P by the projection unit 48B of the projector 48. Specifically, the emission of the projection light for projecting the projection image P is stopped. In a case in which the projection of the projection image P is ended, the supply of power to the power supply unit 48A is cut off to turn off the power supply unit 48A.

As described above, the console 12 according to this embodiment performs control to project the projection image P onto the projection surface 45 in a case in which it is detected that the compression plate 40 is attached to the main body of the mammography apparatus 10 and starts to move. Therefore, according to the console 12 of this embodiment, it is possible to project the projection image P onto the projection surface 45 of the compression plate 40 according to the timing when the user positions the breast.

Second Embodiment

In this embodiment, an aspect in which the projection image P is projected at a timing different from that in the first embodiment will be described.

In addition, the configurations of a mammography apparatus 10 and a console 12 according to this embodiment are the same as those in the first embodiment except that some of the functions of the detection unit 62 in the console 12 are different. Therefore, the description of the same configurations will not be repeated. The detection unit 62 according to this embodiment differs from that in the first embodiment in that it does not have the function of detecting whether or not the compression plate 40 starts to move in the compression direction in which the breast is compressed.

Figure 7:
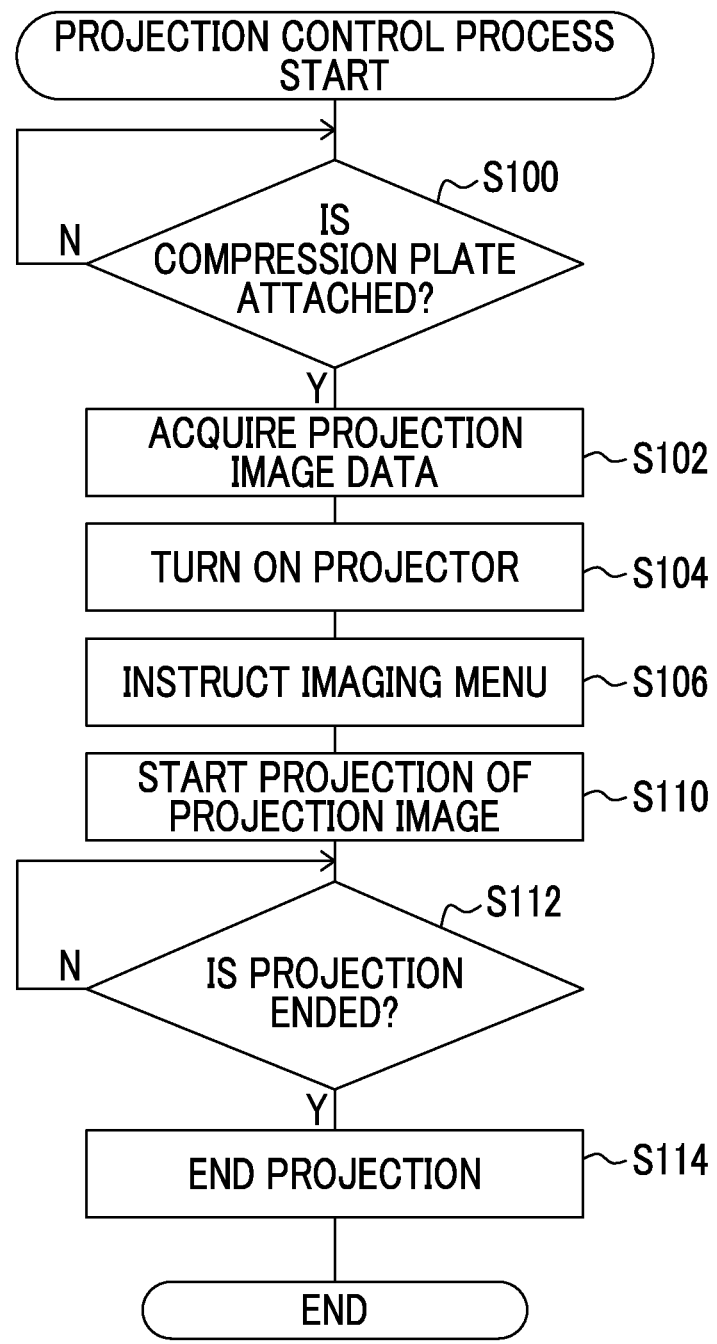
FIG. 7 is a flowchart illustrating an example of the flow of a projection control process according to a second embodiment.

Since a projection control process performed in the console 12 in this embodiment differs from that in the first embodiment, the projection control process according to this embodiment will be described. FIG. 7 is a flowchart illustrating an example of the flow of the projection control process performed in the console 12 according to this embodiment.

As illustrated in FIG. 7, the projection control process according to this embodiment differs from the projection control process (see FIG. 5) according to the first embodiment in that it does not comprise the process in Step S108. Therefore, in the projection control process according to this embodiment, in a case in which the control unit 64 instructs the mammography apparatus 10 on an imaging menu in Step S106, the control unit 64 outputs the projection image data 53 to the mammography apparatus 10 through the I/F unit 54 in the next Step S110.

That is, in the projection control process according to this embodiment, the console 12 performs control to project the projection image P onto the projection surface 45 in a case in which the compression plate 40 is attached to the main body of the mammography apparatus 10 and the mammography apparatus 10 is instructed on the imaging menu. Therefore, according to the console 12 of this embodiment, it is possible to project the projection image P onto the projection surface 45 of the compression plate 40 according to the timing when the user positions the breast.

Third Embodiment

In this embodiment, an aspect in which the projection image P is projected at a timing different from that in the first embodiment will be described.

In addition, the configurations of a mammography apparatus 10 and a console 12 according to this embodiment are the same as those in the first embodiment except that some of the functions of the receiving unit 60 and the detection unit 62 in the console 12 are different. Therefore, the description of the same configurations will not be repeated.

The receiving unit 60 according to this embodiment differs from that in the first embodiment in that it further has a function of receiving a projection start instruction to start the projection of the projection image P. For example, in this embodiment, in a case in which the user wants to start the projection of the projection image P onto the projection surface 45, the user inputs a projection start instruction through the operation unit 26 of the mammography apparatus 10. The mammography apparatus 10 outputs a projection start instruction signal through the I/F unit 24. In a case in which the projection start instruction signal is input to the console 12, the receiving unit 60 receives the projection start instruction to start the projection of the projection image P. The receiving unit 60 outputs projection start information indicating that the projection start instruction has been received to the control unit 64.

Further, the detection unit 62 according to this embodiment differs from that in the first embodiment in that it does not have the function of detecting whether or not the compression plate 40 starts to move in the compression direction in which the breast is compressed.

Figure 8:
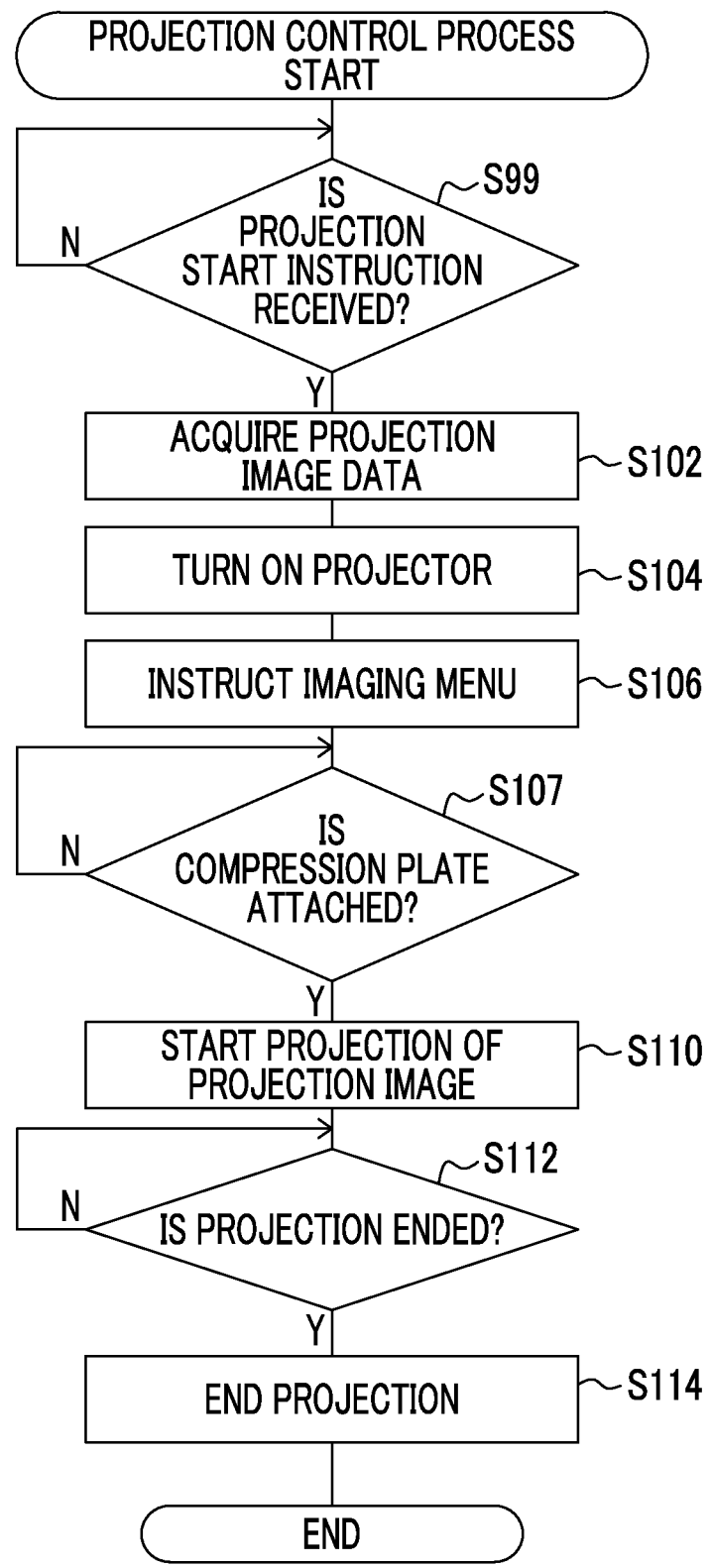
FIG. 8 is a flowchart illustrating an example of the flow of a projection control process according to a third embodiment.

Since a projection control process performed in the console 12 in this embodiment differs from that in the first embodiment, the projection control process according to this embodiment will be described. FIG. 8 is a flowchart illustrating an example of the flow of the projection control process performed in the console 12 according to this embodiment.

As illustrated in FIG. 8, the projection control process according to this embodiment differs from the projection control process (see FIG. 5) according to the first embodiment in that it comprises a process in Step S99 instead of the process in Step S100 and comprises a process in Step S107 instead of the process in Step S108.

As illustrated in FIG. 8, in the projection control process according to this embodiment, first, in Step S99, the control unit 64 determines whether or not the projection start instruction is received. As described above, the determination result in Step S99 is "No" until the receiving unit 60 receives the projection start instruction signal. On the other hand, in a case in which the receiving unit 60 receives the projection start instruction signal, the determination result in Step S99 is "Yes", and the process proceeds to Step S102.

In addition, after the control unit 64 instructs the mammography apparatus 10 on the imaging menu (Step S106), the detection unit 62 determines whether or not the compression plate 40 is attached to the main body of the mammography apparatus 10 in Step S107 as in Step S100 of the projection control process according to the first embodiment. The determination result in Step S107 is "No" until the compression plate identifier is input to the console 12. On the other hand, in a case in which the compression plate identifier is input to the console 12, the determination result in Step S107 is "Yes", and the process proceeds to Step S110.

As described above, the console 12 according to this embodiment performs control to project the projection image P onto the projection surface 45 in a case in which the compression plate 40 is attached to the main body of the mammography apparatus 10 and the projection start instruction is received from the user. Therefore, according to the console 12 of this embodiment, it is possible to project the projection image P onto the projection surface 45 of the compression plate 40 according to the timing when the user positions the breast, as in the first embodiment.

Further, the console 12 according to this embodiment controls the projector 48 which projects the projection image P onto the projection surface 45 of the compression plate 40 such that the projection image P is not projected onto the projection surface 45 in a case in which it is detected that the compression plate 40 is not attached to the main body of the mammography apparatus 10. That is, even though the projection start instruction is received from the user, the projection image P is not projected from the projector 48 in a case in which it is detected that the compression plate 40 is not attached to the main body of the mammography apparatus 10. As described above, in a case in which it is detected that the compression plate 40 is not attached to the main body of the mammography apparatus 10, the console 12 according to this embodiment controls the projector 48 such that the projection image P is not projected. Therefore, it is possible to project the projection image P onto the projection surface 45 of the compression plate 40 at an appropriate timing.

Fourth Embodiment

In this embodiment, an aspect in which the projection image P is projected at a timing different from that in the first embodiment will be described. In addition, in this embodiment, a radiographic image is captured in a different aspect. In each of the above-described embodiments, the aspect in which the mammography apparatus 10 captures one radiographic image has been described. However, in this embodiment, an aspect in which the mammography apparatus 10 captures each of a series of a plurality of radiographic images will be described.

In this embodiment, an aspect in which CC imaging is continuously performed for each of the left and right breasts of the subject will be described as an example of the capture of each of a series of a plurality of radiographic images. Hereinafter, CC imaging for the left breast is referred to as "LCC imaging", and CC imaging for the right breast is referred to as "RCC imaging".

In a case in which the sequential performance of the LCC imaging and the RCC imaging in this order is designated in the imaging menu, first, the LCC imaging is performed with the left breast of the subject compressed by the compression plate 40. In a case in which the LCC imaging ends, the compression of the left breast is released. Then, the RCC imaging is performed with the right breast of the subject being compressed by the compression plate 40. In a case in which the RCC imaging ends, the compression of the right breast is released. Then, the capture of each of a series of a plurality of radiographic images ends.

The configurations of the mammography apparatus 10 and the console 12 according to this embodiment differ from those in the first embodiment in that some of the functions of the detection unit 62 in the console 12 are different and the receiving unit 60 is not comprised. Therefore, the functions of the detection unit 62 which are different from those in the first embodiment will be described.

The detection unit 62 according to this embodiment further has a function of detecting whether or not the compression plate 40 starts to move in the release direction in which the compression of the breast is released. For example, in this embodiment, in a case in which the compression plate driving unit 42 of the mammography apparatus 10 starts to move the compression plate 40 in the release direction, the control unit 20 outputs a release movement start signal indicating the fact to the console 12 through the I/F unit 24. In a case in which the release movement start signal output from the mammography apparatus 10 is input to the console 12, the detection unit 62 detects that the compression plate 40 starts to move in the release direction. In a case in which the detection unit 62 detects that the compression plate 40 starts to move in the release direction, it outputs release movement start information indicating the fact to the control unit 64.

Figure 9:
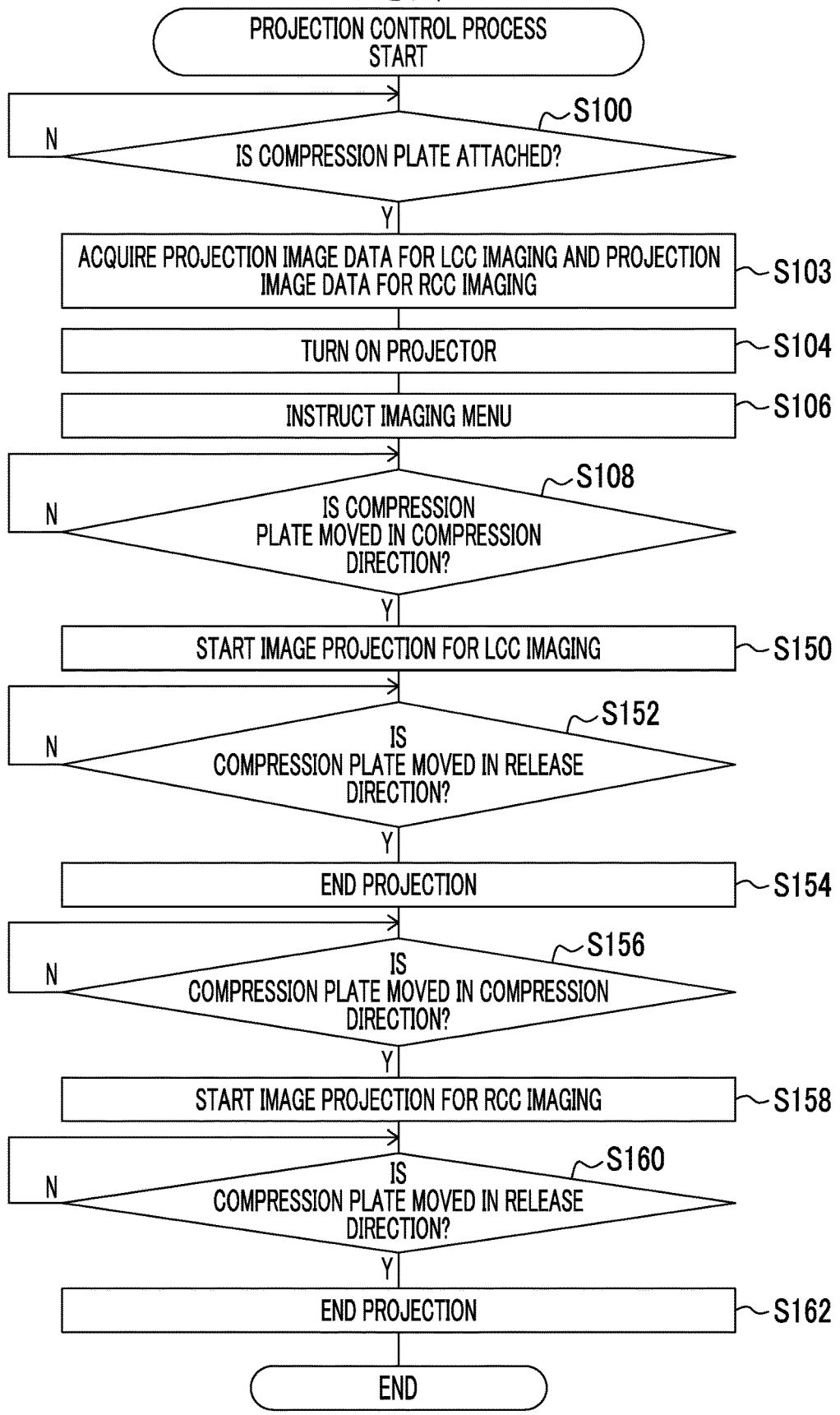
FIG. 9 is a flowchart illustrating an example of the flow of a projection control process according to a fourth embodiment.

Further, since this embodiment differs from the first embodiment in the projection control process performed in the console 12, the projection control process according to this embodiment will be described. FIG. 9 is a flowchart illustrating an example of the flow of the projection control process performed in the console 12 according to this embodiment.

As illustrated in FIG. 9, the projection control process according to this embodiment differs from the projection control process (see FIG. 5) according to the first embodiment in that it comprises a process in Step S103 instead of the process in Step S102.

For example, in this embodiment, each of a plurality of projection image data items indicating projection images P for LCC imaging and a plurality of projection image data items indicating projection images P for RCC imaging which correspond to the types of the compression plates 40 is stored as the projection image data 53 in the storage unit 52 so as to be associated with the compression plate identifier. Therefore, in the projection control process according to this embodiment, as illustrated in FIG. 9, in Step S103, the control unit 64 according to this embodiment acquires the projection image data 53 for LCC imaging and the projection image data 53 for RCC imaging which correspond to the compression plate identifier input from the detection unit 62 from the storage unit 52. In addition, it is preferable that each of the projection image P for LCC imaging and the projection image P for RCC imaging includes an image for displaying information indicating whether an object to be imaged is the left breast or the right breast.

In addition, the projection control process according to this embodiment differs from the projection control process (see FIG. 5) according to the first embodiment in that it comprises processes in Steps S150 to S162 instead of the processes in Steps S110 and S114.

Then, in Step S150, the control unit 64 outputs the projection image data 53 for LCC imaging acquired in Step S103 to the mammography apparatus 10 through the I/F unit 54. In the mammography apparatus 10, in a case in which the projection image data 53 for LCC imaging is input, the control unit 20 performs control to direct the projection unit 48B of the projector 48 to project the projection image P corresponding to the projection image data 53 for LCC imaging. A display image corresponding to the projection image P for LCC imaging is displayed on the projection surface 45 of the compression plate 40 attached to the compression unit 36 of the mammography apparatus 10 by this control.

As described above, the user releases the compression of the left breast in a case in which the LCC imaging ends. Then, in Step S152, the detection unit 62 determines whether or not the compression plate 40 starts to move in the release direction. As described above, the determination result in Step S152 is "No" until the release movement start signal is input to the console 12. On the other hand, in a case in which the release movement start signal is input to the console 12, the determination result in Step S152 is "Yes", and the process proceeds to Step S154.

In Step S154, the control unit 64 outputs an end control signal for ending the projection of the projection image P by the projector 48 to the mammography apparatus 10 through the I/F unit 54. In the mammography apparatus 10, in a case in which the end control signal is input, the control unit 20 ends the projection of the projection image P by the projection unit 48B of the projector 48. Specifically, the emission of the projection light for projecting the projection image P is stopped. Here, the power supply unit 48A of the projector 48 may be kept in the on state.

Then, in a case in which the compression of the left breast is released, the user positions the right breast on the imaging table 30 and moves the compression plate 40 in the compression direction to compress the breast with the compression plate 40. Then, in Step S156, the detection unit 62 determines whether or not the compression plate 40 starts to move in the compression direction as in Step S108. The determination result in Step S156 is "No" until the compression movement start signal is input to the console 12. On the other hand, in a case in which the compression movement start signal is input to the console 12, the determination result in Step S156 is "Yes", and the process proceeds to Step S158.

Then, in Step S158, the control unit 64 outputs the projection image data 53 for RCC imaging acquired in Step S103 to the mammography apparatus 10 through the I/F unit 54. In the mammography apparatus 10, in a case in which the projection image data 53 for RCC imaging is input, the control unit 20 performs control to direct the projection unit 48B of the projector 48 to project the projection image P corresponding to the projection image data 53 for RCC imaging. A display image corresponding to the projection image P for RCC imaging is displayed on the projection surface 45 of the compression plate 40 attached to the compression unit 36 of the mammography apparatus 10 by this control.

As described above, the user releases the compression of the right breast in a case in which the RCC imaging ends. Then, in Step S160, the detection unit 62 determines whether or not the compression plate 40 starts to move in the release direction. As described above, the determination result in Step S160 is "No" until the release movement start signal is input to the console 12. On the other hand, in a case in which the release movement start signal is input to the console 12, the determination result in Step S160 is "Yes", and the process proceeds to Step S162.

In Step S162, the control unit 64 outputs the end control signal for ending the projection of the projection image P by the projector 48 to the mammography apparatus 10 through the I/F unit 54 and then ends the projection control process illustrated in FIG. 9. In the mammography apparatus 10, in a case in which the end control signal is input, the control unit 20 ends the projection of the projection image P by the projection unit 48B of the projector 48. Specifically, the emission of the projection light for projecting the projection image P is stopped. In addition, in a case in which the projection of the projection image P is ended to end the projection control process, the supply of power to the power supply unit 48A is cut off to turn off the power supply unit 48A.

As described above, in a case in which a series of a plurality of radiographic images are captured, the console 12 according to this embodiment performs control to end the projection of the projection image P between the operations of capturing each radiographic image and to project the projection image P corresponding to the capture of each radiographic image onto the projection surface 45 of the compression plate 40. Therefore, according to the console 12 of this embodiment, it is possible to display an appropriate projection image P on the projection surface 45 at an appropriate timing. Further, according to this embodiment, after the projection of the projection image P is ended, the projection image P to be projected is switched. Therefore, it is easy for the user to recognize that the projection image P has been switched.

Fifth Embodiment

The configurations of a mammography apparatus 10 and a console 12 according to this embodiment are the same as those in the first embodiment except that some of the functions of the control unit 64 in the console 12 are different. Therefore, the description of the same configurations will not be repeated.

In some cases, the user is not able to or does not want to project the projection image P depending on the type of the compression plate 40. Examples of the compression plate 40 include a spot compression plate in which the area of a projection surface 45 is small and a compression plate for enlargement imaging in which a focal length is small. For example, in the console 12 according to this embodiment, projection permission information (not illustrated) indicating a compression plate identifier of a type of compression plate onto which the projection of the projection image P is permitted is stored in the storage unit 52 in advance. In addition, unlike this embodiment, a compression plate identifier of a type of compression plate 40 onto which projection is not permitted may be stored in the storage unit 52 in advance. Further, a configuration may be used in which the user can set whether or not to permit projection.

The control unit 64 according to this embodiment further has a function of performing either control to project the projection image P or control not to project the projection image P according to the type of the compression plate 40.

Figure 10:
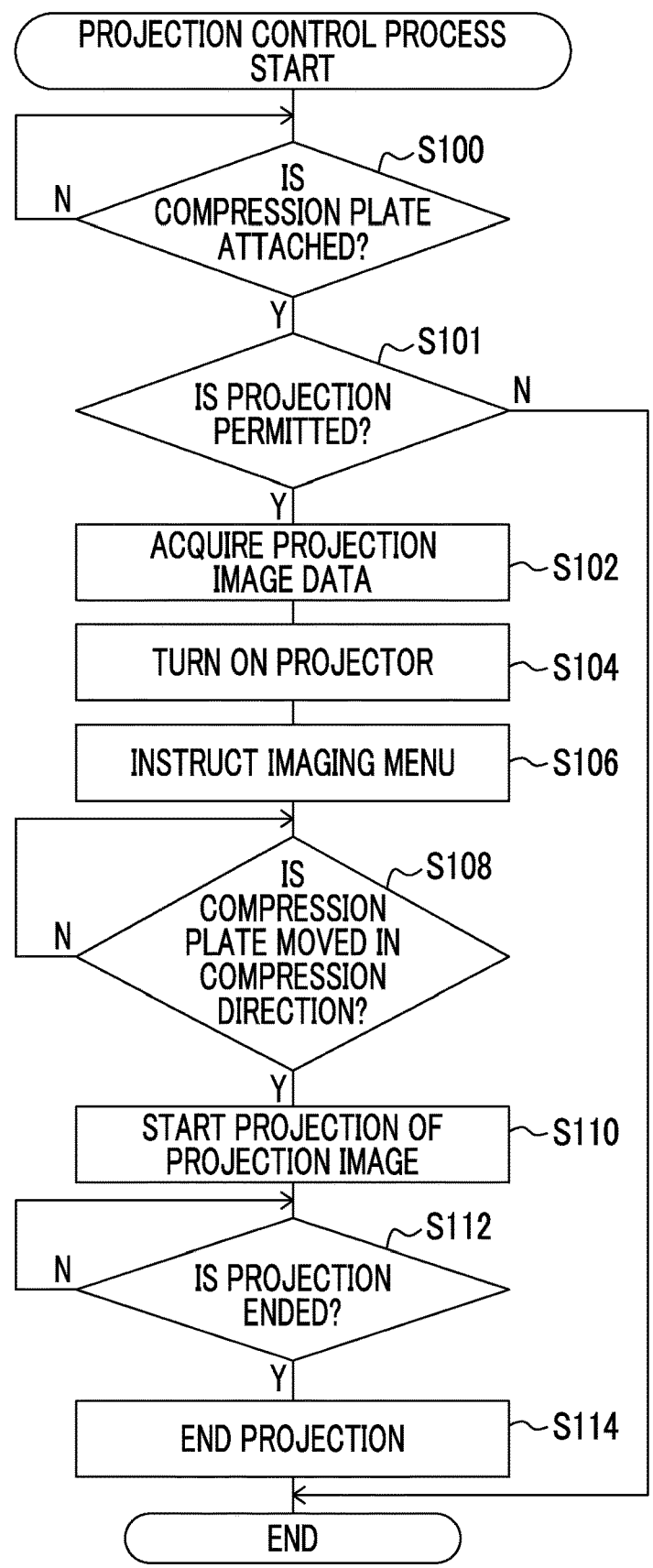
FIG. 10 is a flowchart illustrating an example of the flow of a projection control process according to a fifth embodiment.

Since a projection control process performed in the console 12 in this embodiment differs from that in the first embodiment, the projection control process according to this embodiment will be described. FIG. 10 is a flowchart illustrating an example of the flow of the projection control process performed in the console 12 according to this embodiment.

As illustrated in FIG. 10, the projection control process according to this embodiment differs from the projection control process (see FIG. 5) according to the first embodiment in that it comprises a process in Step S101 between Step S100 and Step S102.

In Step S101 of FIG. 10, the control unit 64 determines whether or not projection is permitted. Specifically, the control unit 64 specifies whether or not the projection permission information stored in the storage unit 52 includes the compression plate identifier input from the detection unit 62. In a case in which the projection permission information includes the compression plate identifier input from the detection unit 62, the determination result in Step S101 is "Yes", and the process proceeds to Step S102. On the other hand, in a case in which the projection permission information does not include the compression plate identifier input from the detection unit 62, the determination result in Step S101 is "No", and the projection control process illustrated in FIG. 10 ends.

As described above, the console 12 according to this embodiment controls whether or not to project the projection image P according to the type of the compression plate 40 attached to the main body of the mammography apparatus 10. Therefore, according to the console 12 of this embodiment, it is possible to prevent the projection image P from being projected onto the compression plate 40 onto which the projection of the projection image P is not required.

As described above, the console 12 according to each of the above-described embodiments comprises the CPU 50A which is at least one processor. The CPU 50A detects whether or not the compression plate 40 that compresses the breast is attached to the main body of the mammography apparatus 10. In addition, in a case in which the CPU 50A detects that the compression plate 40 is attached, it controls the projector 48 which projects the projection image P onto the projection surface 45 of the compression plate 40 such that the projection image P is projected onto the projection surface 45.

As described above, the console 12 according to each of the above-described embodiments performs control to project the projection image P onto the projection surface 45 of the compression plate 40 in a case in which the compression plate 40 is attached to the main body of the mammography apparatus 10. Therefore, according to the console 12 of each of the above-described embodiments, the projection image P is not projected in a case in which the compression plate 40 is not attached to the main body of the mammography apparatus 10. Therefore, according to the console 12 of each of the above-described embodiments, it is possible to project the projection image P onto the projection surface 45 of the compression plate 40 at an appropriate timing.

Further, in each of the above-described embodiments, the aspect in which the console 12 performs control to turn on the power supply unit 48A of the projector 48 in advance before starting the projection of the projection image P has been described. However, the timing when the power supply unit 48A is turned on is not limited to this aspect. For example, the timing may be immediately before the projection of the projection image P is started. Specifically, in the case of the projection control process illustrated in FIG. 5, the timing may be after Step S108. In addition, the power supply unit 48A may be turned on in advance such that the projection image P can be projected, which makes it possible to quickly project the projection image P. On the other hand, in a case in which the timing when the power supply unit 48A is turned on is delayed, it is possible to suppress heat accumulation in, for example, the projector 48.

In each of the above-described embodiments, the aspect in which the projection of the projection image P by the projector 48 is ended in a case in which the user inputs a projection end instruction has been described. However, the timing when the projection of the projection image P is ended is not limited to this aspect. For example, the projection may be ended at the timing when the emission of the radiation R by the radiation source 37R ends.

Further, the configuration for projecting the projection image P in the mammography apparatus 10 described in each of the above-described embodiments is not limited and is not limited to the aspect using the projector 48. Further, in a case in which the projector 48 is applied, the configuration of the projector 48 is not limited. For example, in each of the above-described embodiments, the aspect in which the projection image P projected from the projector 48 is directly projected onto the projection surface 45 has been described. However, the projection image P may be reflected from a mirror or the like to be projected onto the projection surface 45. In this case, the direction in which the projection image P is projected can be adjusted by the mirror or the like. Furthermore, for example, a shutter or the like that blocks the projection light may be provided in front of the projection unit 48B of the projector 48. In this case, the shutter may be opened or closed to control the projection of the projection image P onto the projection surface 45. Specifically, in a case in which the projection of the projection image P is started, control is performed such that the shutter is opened to transmit the projection light. On the other hand, in a case in which the projection of the projection image P is ended, control is performed such that the shutter is closed to block the projection light.

Further, in each of the above-described embodiments, the aspect in which the control unit 64 of the console 12 performs control to turn on the power supply unit 48A of the projector 48 has been described. However, the control unit 64 may not control the power supply unit 48A of the projector 48. For example, the control unit 20 of the mammography apparatus 10 may perform control to turn on the power supply unit 48A of the projector 48 in a case in which the projection image data 53 is input from the console 12.

Further, in each of the above-described embodiments, the aspect in which a projection image for displaying an image for guiding at least one of the shape or position of the breast on the projection surface 45 of the compression plate 40 is applied as the projection image P has been described. However, the projection image P is not limited to this aspect. For example, the projection image P may be a projection image for displaying information related to the subject, such as the name of the subject, and information related to compression, such as compression pressure or the height of the compression plate 40, on the projection surface 45 of the compression plate 40. In addition, the projection image P may be a projection image for displaying a plurality of information items. Further, the projection image P may be a radiographic image of the breast.

Further, in each of the above-described embodiments, the image indicating the skin line of the breast and the position of the nipple in a case in which the standard breast is compressed into an ideal state is applied as the projection image P. However, the projection image P is not limited to this aspect. For example, the projection image P may be the radiographic image of the breast of the same subject captured in the past, an image indicating a skin line generated from the radiographic image captured in the past, or the like. In addition, a method for generating the image indicating the skin line is not particularly limited, and a known technique can be applied. For example, JP2008-086389A discloses a method which examines the density of a radiographic image, detects the position where a density difference is equal to or greater than a predetermined value, and defines a set of pixels having a density difference that is equal to or greater than the predetermined value as a skin line. In addition, for example, JP2010-051456A discloses a method which divides a radiographic image of the breast into a breast region and a blank region on the basis of the density of each pixel of the radiographic image and connects the pixels which are the boundary points between the breast region and the blank region to generate a skin line. Furthermore, the projection image P may be, for example, information related to the current imaging, such as an imaging date and time or a radiographer, information related to the past imaging, such as compression pressure in the past imaging, and information related to the subject, such as the name of the subject. Alternatively, the projection image P may be an image indicating characters or numbers.

Further, in each of the above-described embodiments, the aspect in which the size of the projection image P is equal to or less than the size of the projection surface 45 has been described. However, the size of the projection image P may be equal to or greater than the size of the projection surface 45 of the compression plate 40. That is, the projection image P may be projected onto the imaging surface 30A of the imaging table 30. Furthermore, the projection image P may be projected only on the imaging table 30. Further, for example, the projection image P may be displayed on the wall portion 41B of the compression plate 40.

Further, in each of the above-described embodiments, the aspect in which the console 12 is an example of the control device according to the present disclosure has been described. However, devices other than the console 12 may have the functions of the control device according to the present disclosure. In other words, for example, the mammography apparatus 10 or an external device other than the console 12 may have some or all of the functions of the receiving unit 60, the detection unit 62, and the control unit 64.

Further, in each of the above-described embodiments, for example, the following various processors can be used as the hardware structure of processing units performing various processes such as the receiving unit 60, the detection unit 62, and the control unit 64. The various processors include, for example, a programmable logic device (PLD), such as a field programmable gate array (FPGA), that is a processor whose circuit configuration can be changed after manufacture and a dedicated electric circuit, such as an application specific integrated circuit (ASIC), that is a processor having a dedicated circuit configuration designed to perform a specific process, in addition to the CPU that is a general-purpose processor which executes software (programs) to function as various processing units as described above.

One processing unit may be configured by one of the various processors or a combination of two or more processors of the same type or different types (for example, a combination of a plurality of FPGAs or a combination of a CPU and an FPGA). Further, a plurality of processing units may be configured by one processor.

A first example of the configuration in which a plurality of processing units are configured by one processor is an aspect in which one processor is configured by a combination of one or more CPUs and software and functions as a plurality of processing units. A representative example of this aspect is a client computer or a server computer. A second example of the configuration is an aspect in which a processor that implements the functions of the entire system including a plurality of processing units using one integrated circuit (IC) chip is used. A representative example of this aspect is a system-on-chip (SoC). In this way, various processing units are configured by using one or more of the various processors as a hardware structure.

In addition, specifically, an electric circuit (circuitry) obtained by combining circuit elements, such as semiconductor elements, can be used as the hardware structure of the various processors.

In each of the above-described embodiments, the aspect in which the projection control program 51 is stored (installed) in the ROM 50B in advance has been described. However, the present disclosure is not limited thereto. The projection control program 51 may be recorded on a recording medium, such as a compact disc read only memory (CD-ROM), a digital versatile disc read only memory (DVD-ROM), or a universal serial bus (USB) memory, and then provided. In addition, the projection control program 51 may be downloaded from an external device through a network.

What is claimed is:

1. A control device comprising:
at least one processor that is configured to:
receive instructions to start projection of a projection image from a user;
detect whether or not a compression member which compresses a breast is attached to a main body of a mammography apparatus;
control an image projection unit which projects the projection image onto a projection surface of the compression member such that the projection image is projected onto the projection surface in a case in which it is detected that the compression member is attached;
detect a type of the compression member attached to the main body of the mammography apparatus; and
prohibit projection of the projection image onto the projection surface in a case in which the detected type is a type onto which the projection of the projection image is not permitted.

2. The control device according to claim 1, wherein the at least one processor is further configured to detect whether or not the compression member starts to move in a direction in which the breast is compressed, and to perform control to project the projection image onto the projection surface in a case in which it is detected that the compression member is attached and starts to move.

3. The control device according to claim 1, wherein the at least one processor is configured to instruct the mammography apparatus on an imaging menu related to the capture of an image of the breast, and to perform control to project the projection image onto the projection surface in a case in which the compression member is attached and the mammography apparatus is instructed on the imaging menu.

4. The control device according to claim 1, wherein the at least one processor is configured to receive a projection start instruction to start the projection of the projection image onto the projection surface, and to perform control to project the projection image onto the projection surface in a case in which the compression member is attached and the projection start instruction is received.

5. The control device according to claim 1, wherein the at least one processor is configured to receive a projection end instruction to end the projection of the projection image onto the projection surface, and to perform control to end the projection of the projection image onto the projection surface in a case in which the projection end instruction is received.

6. The control device according to claim 1, wherein, after controlling the image projection unit such that the projection image is capable of being projected, the at least one processor is configured to perform control to project the projection image onto the projection surface.

7. The control device according to of claim 1, wherein, in a case in which the mammography apparatus captures each of a series of a plurality of radiographic images, the at least one processor is configured to perform control to project, onto the projection surface, the projection image corresponding to each imaging operation, which corresponds to each of the plurality of radiographic images, in each imaging operation.

8. The control device according to claim 1, wherein the at least one processor is further configured to perform control to project the projection image onto the projection surface in a case in which the detected type is a type onto which the projection of the projection image is permitted.

9. A control device comprising:

at least one processor that is configured to:

receive instructions to start projection of a projection image from a user;

detect whether or not a compression member which compresses a breast is attached to a main body of a mammography apparatus;

control an image projection unit which projects the projection image onto a projection surface of the compression member such that the projection image is projected onto the projection surface in a case in which it is detected that the compression member is attached; and control the image projection unit such that the projection image is not projected in a case in which it is detected that the compression member is not attached.

10. A control method comprising:

receiving instructions to start projection of a projection image from a user;

detecting whether or not a compression member which compresses a breast is attached to a main body of a mammography apparatus;

controlling an image projection unit which projects the projection image onto a projection surface of the compression member such that the projection image is projected onto the projection surface in a case in which it is detected that the compression member is attached;

detecting a type of the compression member attached to the main body of the mammography apparatus; and prohibiting projection of the projection image onto the projection surface in a case in which the detected type is a type onto which the projection of the projection image is not permitted.

11. A control method comprising:

receiving instructions to start projection of a projection image from a user;

detecting whether or not a compression member which compresses a breast is attached to a main body of a mammography apparatus;

controlling an image projection unit which projects the projection image onto a projection surface of the compression member such that the projection image is projected onto the projection surface in a case in which it is detected that the compression member is attached; and controlling the image projection unit such that the projection image is not projected in a case in which it is detected that the compression member is not attached.

12. A non-transitory computer-readable storage medium storing a control program that causes a computer to perform a process comprising:

receiving instructions to start projection of a projection image from a user;

detecting whether or not a compression member which compresses a breast is attached to a main body of a mammography apparatus;

controlling an image projection unit which projects the projection image onto a projection surface of the compression member such that the projection image is projected onto the projection surface in a case in which it is detected that the compression member is attached;

detecting a type of the compression member attached to the main body of the mammography apparatus; and prohibiting projection of the projection image onto the projection surface in a case in which the detected type is a type onto which the projection of the projection image is not permitted.

13. A non-transitory computer-readable storage medium storing a control program that causes a computer to perform a process comprising:

receiving instructions to start projection of a projection image from a user;

detecting whether or not a compression member which compresses a breast is attached to a main body of a mammography apparatus;

controlling an image projection unit which projects the projection image onto a projection surface of the compression member such that the projection image is projected onto the projection surface in a case in which it is detected that the compression member is attached; and controlling the image projection unit such that the projection image is not projected in a case in which it is detected that the compression member is not attached.

* * * * *